United States Patent [19]

Legros et al.

[11] Patent Number: 5,244,678
[45] Date of Patent: Sep. 14, 1993

[54] PHARMACEUTICAL COMPOSITION CONTAINING A LOCAL ANESTHETIC AND/OR CENTRALLY ACTING ANALGESIC ENCAPSULATED IN LIPOSOMES

[75] Inventors: Franz Legros, Bruxelles; Jean-Marie Ruysschaert, Rhode-St Genese, both of Belgium

[73] Assignee: Ire-Celltarg S.A., Fleurus, Belgium

[21] Appl. No.: 643,107

[22] Filed: Jan. 22, 1991

Related U.S. Application Data

[63] Continuation of Ser. No. 323,147, Mar. 10, 1989, abandoned, which is a continuation of Ser. No. 2,896, Jan. 13, 1987, abandoned.

[30] Foreign Application Priority Data

Jan. 14, 1986 [FR] France .............................. 86 00434

[51] Int. Cl.$^5$ ................... A61K 37/22; A61K 31/445
[52] U.S. Cl. ..................................... 424/450; 514/330
[58] Field of Search ................ 514/330; 424/417, 415, 424/43, 41, 450

[56] References Cited

U.S. PATENT DOCUMENTS

| | | | |
|---|---|---|---|
| 3,993,754 | 11/1976 | Rahman et al. | 424/450 |
| 4,186,183 | 1/1980 | Steck et al. | 264/4.1 |
| 4,419,348 | 12/1983 | Rahman et al. | 514/34 |
| 4,622,219 | 11/1986 | Haynes | 424/450 |

FOREIGN PATENT DOCUMENTS 0152379 8/1985 European Pat. Off. .

OTHER PUBLICATIONS

Chemical Abstracts, vol. 94, 1981, p. 66, No. 58303h, by T. Okano et al., "Duration of the local anesthetic action of dibucaine by liposomes and its mechanism" & Yakugaku Zasshi 1980, 100(11), 1097-103.
Chemical Abstracts, vol. 96, 1982, p. 136, No. 116500z, Columbus, Ohio; "Enhanced analgesic activity of liposomised Met-enkephalin analog" & Indian J. Biochem. Biophys. 1981, 18(6), 440-1.
Chemical Abstracts, vol. 86, 1977, p. 26, No. 165153r, Columbus, Ohio, by P. L. Yeagle et al., "Molecular dynamics of the local anesthetic tetracaine in phospholipid vesicles" & Biophys. Acta 1977, 465(2), 173-8.
Biochimca et Biophsyica Acta, vol. 799, 1984, pp. 195-198, Elsevier Science Publishers B.V.; Naomi Kraus-Friedman et al.; "Lipsome encapsulated tetracaine lowers bood glucose".
Chemical Abstract 104: 39720a (1986).

Primary Examiner—Zohreh A. Fay
Attorney, Agent, or Firm—Jacobson, Price, Holman & Stern

[57] ABSTRACT

The present invention relates to a pharmaceutical composition containing a local anesthetic or a centrally acting analgesic, comprising a lipophilic portion, the anesthetic or analgesic being encapsulated in liposomes.

2 Claims, 1 Drawing Sheet

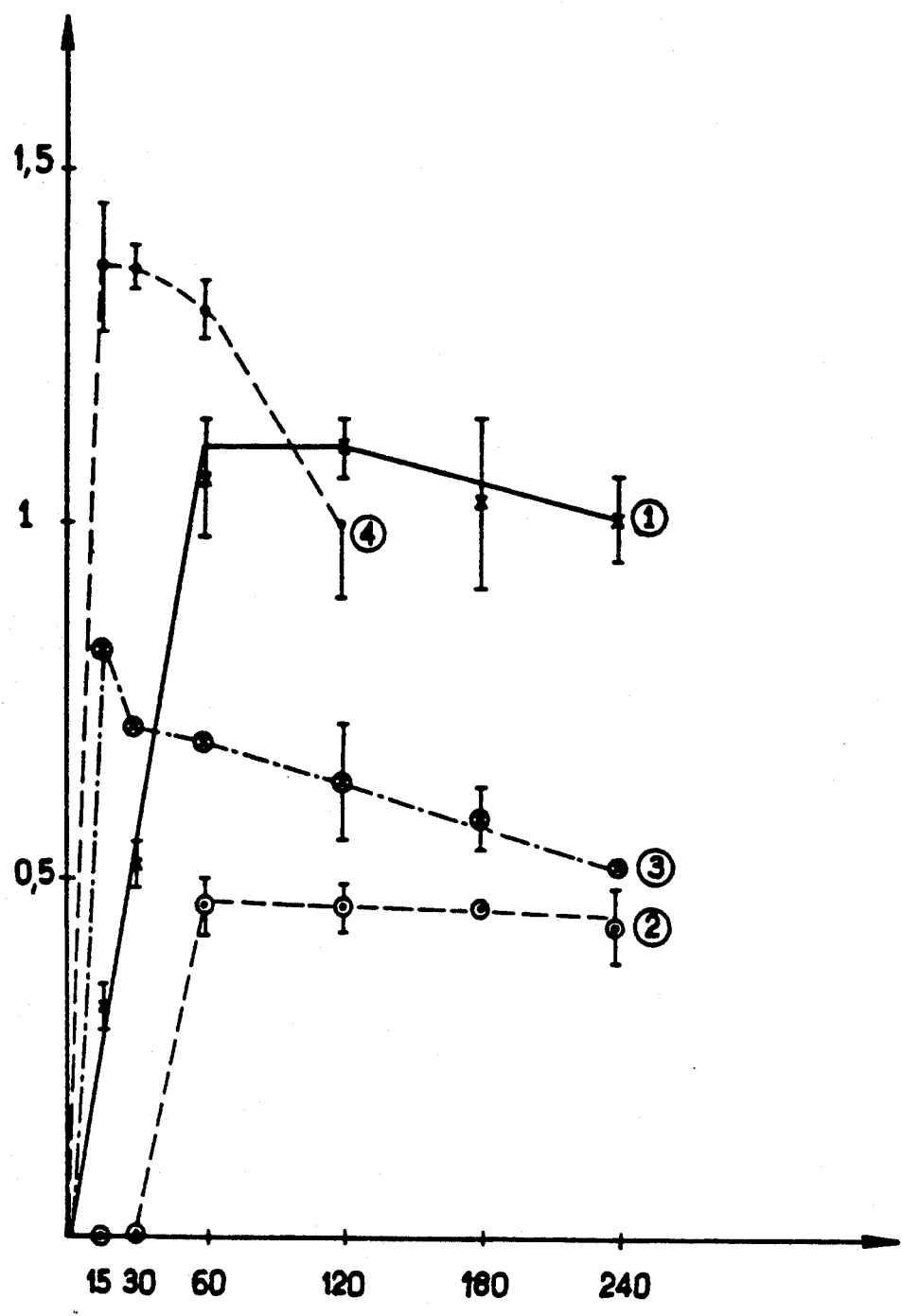

PHARMACEUTICAL COMPOSITION CONTAINING A LOCAL ANESTHETIC AND/OR CENTRALLY ACTING ANALGESIC ENCAPSULATED IN LIPOSOMES

This application is a continuation of application Ser. No. 07/323,147, filed Mar. 10, 1989 now abandoned which is a continuation of application Ser. No. 07/002,896, filed Jan. 13,1987, now abandoned.

The present invention relates to pharmaceutical compositions for anesthesia, and principally peridural anesthesia. Peridural anesthesia is a local-regional conduction anesthesia carried out by the injection of a local anesthetic into the peridural space.

This space is situated between the dura mater and the osteoligamentous walls of the vertebral canal. It is closed at the top by the dura mater, which adheres intimately to the periphery of the occipital foramen. At the bottom, the dura mater terminates at the level of the second sacral vertebra. At this level, the terminal film separates and adheres to the coccyx. The peridural space thus extends from the occipital foramen to the sacrococcygeal membrane. It contains a loose celluloadipose tissue, the roots of spinal nerves, spinal arteries, vertebral venous plexuses, and lymph ducts.

The principle of peridural analgesia has been known for a very long time, since this technique is almost as old as local cocaine anesthesia.

Local anesthetics act on the nerve fiber, interfering with the processes of excitation-conduction. However, the nerve fibers are unequally sensitive to the action of local anesthetics. Initially, the neurovegetative fibers are affected (sympathetic block), then the sensory fibers (the sensations disappearing in the order: pain, heat, touch); the motor fibers are the last to be affected.

Many substances possess local anesthetic properties, but are not used because they do not possess all the qualities of a good local anesthetic.

And especially, among anesthetics derived from cocaine, there are variations in the intensity of the action according to the product. Thus, for example, bupivacaine affects motor fibers to only a small extent, if at all.

Remedying the insufficiently powerful action of anesthetics by increasing the doses would lead to certain toxicity. In effect, a not insignificant percentage of the anesthetic, even when administered peridurally, travels via the blood stream, and/or the spinal and then the cerebrospinal fluid, and finds its way to various organs, especially the heart and the liver and/or the central nervous system.

Thus, if a stronger dose of anesthetic were injected in order to overcome an excessively weak or insufficiently long-lasting action, this would run the risk of producing very serious or even irremediable toxic effects, ranging, for example, from a fall in the bloodpressure to disorders of heart rate or even to cardiac arrest.

The present invention proposes a solution for remedying the abovementioned disadvantages.

In effect, the present invention relates to pharmaceutical compositions which contain a local anesthetic and/or a centrally acting analgesic, comprising a lipophilic portion, the anesthetic or analgesic being encapsulated in liposomes.

In effect, the long-lasting action of lipophilic anesthetics administered in the peridural space in watersoluble form has been attributed essentially to their uptake and sequestration by the adipose tissue.

In point of fact, liposomes are vesicles consisting of a double layer of phospholipids in an aqueous solution, with their hydrophilic portions in contact with the water on the outside and their hydrophobic portions inside the bilayers.

Specifically, liposoluble molecules can be trapped within the phospholipid bilayers.

In this method, lipophilic anesthetics are candidates for trapping in the liposomes, and the same can apply to other active principles which can be administered peridurally, such as centrally acting analgesics of the morphine type.

Among these anesthetics, there should be mentioned local anesthetics, chosen from benzoic acid derivatives, anilide derivatives or cocaine derivatives, as well as centrally acting analgesics, morphine or morphine derivatives.

Although the liposomes used in these compositions can be varied in nature and, in particular, multilamellar (MLV) or unilamellar (SUV), they will preferably be mutlilamellar liposomes.

The nature of the components taking part in the construction of the liposomes may influence the modulation of the activity of the encapsulated active principles, but, regardless of the composition, the advantageous effects which will be described below will remain essentially unaltered.

By way of example, a phosphadidylcholine (Pc)/cholesterol (Ch) composition, in particular, in a mole ratio 4:3 will be especially advantageous.

The preparation of the liposomes according to the invention can be performed according to known methods, the active principle preferably being encapsulated at the time of formation of the liposomes.

To this end, the active principle, preferably in the form of a liposoluble base, is dissolved in chloroform with the two liposome components, e.g. egg Pc and Ch, respectively, in a mole ratio of 4:3.

The respective amounts of phospholipids and active principle can vary.

According to a favored embodiment of the liposomes, according to the present invention, approximately 60 mg of lipids and approximately 4 to 5 mg of anesthetic in the form of liposoluble base are dissolved in chloroform.

This mixture is evaporated under an atmosphere of nitrogen, and then under vacuum overnight.

The formation of the liposomes then varies according to whether it is desired to obtain MLVs or SUVs. In the former case, approximately 3 ml of 0.3M Tris-HCL buffer, pH 8, are added to the lipid film obtained, and 5 centrifugations are performed in the same buffer; in the second case, sonication is performed for approximately 15 minutes at 65 W.

The liposomes with the anesthetic thereby incorporated are administered in the form of pharmaceutical compositions containing, in addition, an acceptable carrier for injection, especially for peridural injection.

Compositions according to the present invention are principally usable in injectable form, that is to say with an excipient which is compatible with the liposomes and the route used; this may, most frequently, be physiological saline.

The compositions according to the invention can also contain active principles other than anesthetics or analgesics, for example, in the case of bupivacaine, it is possible to use epinephrine in combination, and this may also be encapsulated if necessary.

Although the epidural route is preferred, other routes can be envisaged, depending on the objective sought (surgical anesthesia or pure analgesia).

Under these conditions, the dosages may vary according to the weight and condition of the patient, and also according to the objective being pursued; this will frequently be left to the evaluation of the anesthetist or the practioner.

Surprisingly, the experiments performed with the compositions according to the invention have shown that the encapsulation of the drug in the liposomes leads to a superior anesthetic action compared with the non-encapsulated drug, to a longer-lasting action at equal doses, to the possibility of reducing the doses to obtain a similar effect and to a decrease in the side effects.

The present invention also relates to a process by means of which the action of a local anesthetic and/or a centrally acting analgesic may be made longer lasting, wherein a pharmaceutical composition containing such an active principle encapsulated in liposomes is administered peridurally.

The examples and figures below are given purely for guidance, and enable other characteristics and advantages of the present invention to be illustrated.

BRIEF DESCRIPTION OF DRAWING

The single FIGURE shows the results relating to the blood kinetics after administration of:

SUV based on $^{14}$C-labeled Pc, represented by the curve 1 (x—x),

MLV containing $^3$H-labeled bupivacaine, represented by the curve 2 (O—O), bupivacaine combined with adrenaline, represented by the curve 3 (.—.), bupivacaine alone, represented by the curve 4 (.—.).

EXAMPLE 1

Preparation of the liposomes and incorporation of bupivacaine (1-1) Preparation of the liposomes alone The liposomes, an essential part of the pharmaceutical compositions according to the present invention, are prepared by known techniques. They preferably contain two main compounds, namely, egg phosphatidylcholine (Pc) and cholesterol (Ch), in a mole ratio of 4:3 and at a total lipid concentration of approximately 20 mg/ml.

According to a preferred process for preparing the liposomes according to the present invention, the egg Pc and the Ch are mixed in a chloroform solution, which is evaporated under nitrogen, and then under vacuum, overnight.

The liposomes are then formed in the following manner: depending on whether approximately 3 ml of 0.3M phosphate buffer at a pH of approximately 7.4 are added, or sonication is performed for 15 minutes at 65 W, either multilamellar liposomes (MLV) or unilamellar liposomes (SUV) are obtained, respectively.

The liposomes obtained are administered in the peridural space in the form of pharmaceutical compositions containing, in addition, an acceptable support, by way of reference liposomes.

(1-2) Preparation of bupivacaine-containing liposomes 4.5 mg of soluble bupivacaine base are added to 60 mg of lipids composed of egg Pc and Ch in a mole ratio of 4:3, and this mixture is dissolved in chloroform.

After evaporation under an atmosphere of nitrogen and under vacuum overnight, MLV liposomes are formed by adding 3 ml of 0.3M Tris-HCl buffer, pH 8, and by 5 centrifugations at 5000 rpm in the same buffer.

EXAMPLE 2

Biodistribution and pharmacokinetics of the liposomes which have incorporated bupivacaine, administered peridurally The study related to MLVs which had incorporated bupivacaine, in the proportion of 4.5 mg of soluble bupivacaine base for 60 mg of lipids containing egg Pc and Ch in the proportion of a mole ratio of 4:3 [see Example (1-2)].

Bupivacaine has been used in chemistry since 1963, and possesses the following formula:

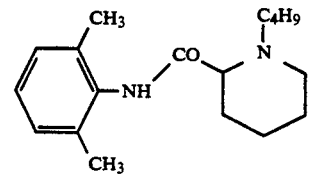

The formation of MLVs takes place by adding 3 ml of 0.3M Tris-HCl buffer, pH 8, followed by 5 centrifugations at 5000 g in the same buffer.

0.2 ml of the centrifugation pellet are administered peridurally to rabbits, under the same conditions as in Example 1.

By way of control, 4.5 mg of bupivacaine for clinical use (Marcaine®-Astra-5% strength hydrochloride solution) is administered under the same conditions with or without adrenaline, and with the addition of 0.01 mCi of [$^3$H]bupivacaine, this combination being present in a total 0.2 ml of solution.

Likewise, by way of control, SUVs without bupivacaine are administered in the course of this study, under the conditions stated in Example 1.

The rabbits' blood is sampled 15, 30, 60, 120, 180 and 240 minutes after the injection.

The results are expressed as a percentage of the injected dose (ID) in the whole blood.

The animals are sacrificed 120 and 240 minutes after the injection, and the organs and tissues are sampled under the same conditions as those of Example 1.

(2-1) The results relating to the blood kinetics are shown in the FIGURE.

The highest blood levels (1.4% of the injected dose) are attained in the 15 to 60 minutes following the injection of bupivacaine alone.

When adrenaline is added to the bupivacaine, the blood peak is 0.8%. This is due to the vasoconstrictive action of the adrenaline reducing the passage through the endothelium of the capillaries which pass through the peridural space. Under this effect, the circulating levels are even lower than those observed after administration of SUV liposomes without adrenaline.

For the bupivacaine-MLV liposomes, the lowest blood levels are found (±0.45%). In addition, the presence of bupivacaine in the blood is only noted 60 minutes after the injection.

From the standpoint of passage into the circulation and systemic (cardiac) toxic effects which are its consequence, the bupivacaine-MLV liposome hence possesses greater safety than that of the anesthetic forms currently used, and also greater safety than that of the SUV liposomes.

(2-2) The results relating to the urinary excretion appear in Table I

Radioactivity excreted in the urine (ID×$10^2$) 2 hours after the peridural injection of [$^3$H]Ch-labeled SUV, of MLV which has integrated $^3$H-labeled bupivacaine, or of non-encapsulated bupivacaine. Mean±standard deviation; the number in brackets=the number of animals.

TABLE I

| [$^3$H]cholesterol SUV | [$^3$H]bupivacaine-MLV | Bupivacaine |
| --- | --- | --- |
| 0 | 5.808 ± 0.175 (3) | 11.633 ± 0.518 (3) |

The amount of bupivacaine, or of the products of its metabolism, excreted is only half as great after peridural injection of bupivacaine-MLV as after that of bupivacaine. This is to be associated with the passage into the general circulation and with the blood levels.

(2-3) Results relating to the cerebrospinal fluid appear in Table II:

Labeling of the cerebrospinal fluid (ID in 1.5 ml×$10^3$) 2 and 4 hours after the peridural injection of [$^3$H]Ch SUV, of MLV which has incorporated [$^3$H]bupivacaine, or of non-encapsulated bupivacaine. Mean±standard deviation; number in brackets=number of animals.

TABLE II

|  | [$^3$H]cholesterol SUV | [$^3$H]bupivacaine-MLV | Bupivacaine |
| --- | --- | --- | --- |
| 2 hours | 0 (3) | 0 (3) | 0.256 + 0.018 (3) |
| 4 hours | 0 (3) | 0 (3) | 0.111 ± 0.003 (3) |

A complete absence of labeling is observed after peridural injection of SUV and MLV, and the presence of radioactive molecules after injection of bupivacaine, this being a known phenomenon, responsible for the toxic manifestations at the level of the central nervous system. The liposomes encapsulating the anesthetic hence avoid this toxicity.

(2-4) Results relating to the liver and cardiac levels appear in Table III:

Biodistribution of [$^3$H]Ch SUV, of MLVS which have integrated [$^3$H]bupivacaine, and of bupivacaine, in the liver and heart 4 hours after the peridural injection (ID×$10^2$).

Mean±standard deviation

Number in brackets=number of animals.

TABLE III

| Organ | [$^3$H]cholesterol SUV | [$^3$H]bupivacaine-MLV | Bupivacaine |
| --- | --- | --- | --- |
| Liver | 10.353 ± 1.009 (3) | 7.449 ± 1.185 (3) | 20.477 ± 1.458 (3) |

TABLE III-continued

| Organ | [$^3$H]cholesterol SUV | [$^3$H]bupivacaine-MLV | Bupivacaine |
| --- | --- | --- | --- |
| Heart | 0.605 ± 0.037 (3) | 0.500 ± 0.030 (3) | 2.142 ± 0.301 (3) |

The cardiac levels are lower after injection of MLV than after that of SUV (associated with the circulating levels). The cardiac accumulation of encapsulated bupivacaine represents only 25% of that observed after injection of bupivacaine. This is very important for avoiding the cardiotoxic risks of anesthesia.

The liver levels are also the lowest after injection of bupivacaine-MLV (again, to be connected with the passage into the circulation).

(2-5) The results relating to the concentration in the nervous tissues appear in Table IV.

Uptake of [$^3$H]Ch SUV, of MLV which has integrated [$^3$H]bupivacaine, and of bupivacaine, by the nervous tissues 2 and 4 hours after the peridural injection (ID in 1 g×$10^3$). Mean±standard deviation; number in brackets=number of animals.

TABLE IV

| Tissue | Time | [$^3$H]cholesterol SUV | [$^3$H]bupivacaine-MLV | Bupivacaine |
| --- | --- | --- | --- | --- |
| Nerve | 2 hrs | NT | NT | NT |
| roots | 4 hrs | 0.278 ± 0.042 (3) | 2.535 ± 0.145 (3) | 0.153 ± 0.023 (3) |
| Lumbar | 2 hrs | 0.303 ± 0.032 (3) | 1.936 ± 0.130 (3) | 0.411 ± 0.094 (3) |
| marrow | 4 hrs | 0.303 ± 0.031 (3) | 0.718 ± 0.002 (3) | 0.169 ± 0.046 (3) |
| Cauda | 2 hrs | 0.423 ± 0.066 (3) | 1.209 ± 0.187 (3) | 0.485 ± 0.057 (3) |
| equina | 4 hrs | 0.374 ± 0.072 (3) | 1.806 ± 0.281 (3) | 0.132 ± 0.035 (3) |
| Sciatic | 2 hrs | 0.307 ± 0.035 (3) | 2.143 ± 0.077 (3) | 0.281 ± 0.026 (3) |
| nerve | 4 hrs | 0.500 ± 0.060 (3) | 1.018 ± 0.213 (3) | 0.132 ± 0.028 (3) |
| Brachial | 2 hrs | 0.277 ± 0.038 (3) | 1.787 ± 0.049 (3) | 0.295 ± 0.048 (3) |
| plexus | 4 hrs | 0.373 ± 0.032 (3) | 0.775 ± 0.091 (3) | 1.136 ± 0.008 (3) |

In all cases, the highest concentrations are found for bupivacaine encapsulated in MLV, 2 or 4 hours after the injection.

The order of concentrations is MLV>SUV>-bupivacaine in all cases.

These results underline the high tropic effect of MLVs for the nerve roots, the sciatic nerve and the brachial plexus. This suggests that there is:

a superior anesthetic action for the encapsulated drug;

a possibility of reducing the doses to obtain a similar effect a longer-lasting action at equal doses.

In addition, as regards, now, the effects observed, a motor block of the hind legs was observed after peridural administration (S2–S3 level) of bupivacaine encapsulated in MLV. The bupivacaine used today in anesthesia blocks the sensory fibers and not the motor fibers. This suggests that there is better penetration of the encapsulated drug into the nerve fibers, compared with the non-encapsulated drug.

Finally, as regards the investigation of possible toxicity at the nerve fiber level, an anatomopathological investigation was performed at the level of the nerve roots, the sciatic nerve, the brachial plexus, the cauda equina and the meninges, 5 hours after the peridural injection of MLV. No effect was observed at the histological level. These results are promising, but it should be noted that, in the use of anesthetics, nerve effects can appear 4 to 6 weeks after injection.

EXAMPLE 3

Analgesic effect of a liposomal composition according to the invention

The analgesic effect is measured by the increase in the threshold of the pain induced by an electric shock to the tail of rats.

(3-1) Liposomal composition

Lipid film: Egg Pc/Chol, 4:3–60 mg of lipids (equivalent to 43.26 mg of egg Pc and 16.74 mg of Chol)+5 mg of bupivacaine base in lyophilized, liposoluble form. Formation of the liposomes: Suspension of the lipid film in the form of multilamellar liposomes in a 0.3M Tris-HCl buffer, pH 8 (3 ml). The liposomal suspension is centrifuged, and the liposomal pellet is injected as it is (0.5 ml) under the skin, in the rat's tail at a point $S_2$.

(3-2) Measurement of the pain threshold

The pain threshold is measured by electrical excitation at $S_2$, and then at $S_1$ ($S_1$, situated 5 cm downstream from the injection point, serves for taking a reference with respect to the injection point, and also for measuring the possible diffusion of the product injected at $S_2$).

Before the injection of the bupivacaine-containing liposomes, the pain threshold, at both $S_2$ and $S_1$, is from 5 to 10 mV (measurements performed every 10 minutes during 1 hour). In the hour which follows the injection, the pain threshold rises at $S_2$. This analgesic effect is maintained for 48 hours. The threshold rises approximately 2- to 5-fold during the 5 to 6 hours which follow the injection. On the following day and the day after that, it is equal to twice the base threshold. The analgesic effect hence persists for ±48 hours (delayed effect or prolonged effect of the bupivacaine-containing liposomes). The statistical significance of the phenomenon was demonstrated by Student's test and the Wilcoxson test (n=6).

Sometimes, after several hours, the pain threshold also rises at $S_1$, and remains equal to twice the base threshold for 48 hours. This indicates possible diffusion of the product from the injection point.

(3-3) Controls

Injection of 5 mg of free bupivacaine (Marcaine of Astra-Nobel) at $S_2$. The pain threshold rises rapidly (less than one hour) at $S_2$, to 5 to 10 times the base value, but the analgesic effect disappears after 6 to 8 hours, as is traditionally described by clinicians.

Injection of the buffer: no modification of the pain threshold during 72 hours.

(3-4) Efficiency of encapsulation and stability of the preparation

In Tris buffer at pH 8, bupivacaine is at its pK (8.1). The maximum theoretical capacity for encapsulation by insertion in the liposomal bilayers is hence 50%. Actual measurements with the liposomes prepared from Lipid films to which 0.1 mCi of [$^3$H]bupivacaine was added indicate an efficiency of 40%. This means that, starting with 5 mg in the lipid films, 2 mg have been encapsulated in the limposomal bilayers.

When stored at 37° C. in the buffer, the liposomal preparation remains stable for 10 days. Measurements beyond this time have not yet been performed.

(3-5) Comments

The controls by injection of free bupivacaine are overestimated, since the amounts administered correspond to those incorporated in the lipid films, but not to those effectively encapsulated. In effect, the liposomal encapsulation starting with 5 mg of liposoluble bupivacaine is 2 mg. The dose administered was hence 2 mg of encapsulated bupivacaine, whereas the pain threshold in the control rats was measured with 5 mg of free bupivacaine.

Sterile liposomal preparations of bupivacaine have been obtained for the purpose of performing toxicity studies:

1. Possible local toxicity, by subcutaneous injection of the sterile solutions into rabbits' ears: inflammation, granuloma formation, pyrogenic effect.

2. Nerve toxicity, by depositing the sterile solutions at the level of the rat sciatic nerve and anatomopathological studies after 6 to 8 weeks.

3. Determination of the plasma levels of bupivacaine during the 72 hours which follow subcutaneous administration to rats.

We claim:

1. A method of administering bupivacaine having reduced toxicity, comprising encapsulating bupivacaine in multilamellar liposomes, and then injecting peridurally an anesthetically effective amount of the encapsulated bupivacaine.

2. A method of claim 1, wherein said multilamellar liposomes comprise egg phosphatidylcholine and cholesterol in a molar ratio of about 4:3.

* * * * *